US006884743B2

(12) United States Patent
Müller et al.

(10) Patent No.: US 6,884,743 B2
(45) Date of Patent: Apr. 26, 2005

(54) CATALYST FOR EPOXIDATION REACTIONS

(75) Inventors: Ulrich Müller, Neustadt (DE); Georg Krug, Mörlenbach (DE); Peter Bassler, Viernheim (DE); Hans-Georg Göbbel, Kallstadt (DE); Peter Rudolf, Ladenburg (DE); Joaquim Henrique Teles, Otterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 73 days.

(21) Appl. No.: 10/243,669

(22) Filed: Sep. 16, 2002

(65) Prior Publication Data

US 2004/0053772 A1 Mar. 18, 2004

(51) Int. Cl.$^7$ .............................. B01J 29/06; B01J 29/89
(52) U.S. Cl. .............................. 502/64; 502/60; 502/71; 502/77; 423/702; 423/704; 423/705; 423/707
(58) Field of Search .............................. 502/60, 64, 71, 502/77; 423/702, 704, 705, 707

(56) References Cited

U.S. PATENT DOCUMENTS

| | | | |
|---|---|---|---|
| 4,410,501 A | | 10/1983 | Taramasso et al. |
| 4,431,621 A | | 2/1984 | Taramasso et al. |
| 4,666,692 A | | 5/1987 | Taramasso et al. |
| 5,063,038 A | * | 11/1991 | Kirker et al. ............... 423/703 |
| 5,160,500 A | | 11/1992 | Chu et al. |
| 5,336,393 A | * | 8/1994 | Takatsu et al. ........ 208/120.15 |
| 5,688,484 A | * | 11/1997 | Saxton et al. ............... 423/700 |
| 5,919,430 A | * | 7/1999 | Hasenzahl et al. .......... 423/702 |
| 6,054,112 A | * | 4/2000 | Hasenzahl et al. .......... 423/705 |
| 6,491,861 B1 | * | 12/2002 | Grosch et al. .............. 264/628 |
| 2001/0041162 A1 | | 11/2001 | Schoebrechts |

FOREIGN PATENT DOCUMENTS

| | | |
|---|---|---|
| EP | 1 364 705 A1 | 1/2002 |
| WO | WO 98/55229 | 12/1998 |
| WO | WO 02/060580 A1 | 8/2002 |

OTHER PUBLICATIONS

A. Thangaraj et al., "Studies on the Synthesis of Titanium Silicalite, TS–1," *Zeolites*, 1992, vol. 12, Nov./Dec., pp. 943–950.

* cited by examiner

*Primary Examiner*—Christina Ildebrando
(74) *Attorney, Agent, or Firm*—Oblon, Spivak, McClelland, Maier & Neustadt, P.C.

(57) ABSTRACT

The present invention relates to the manufacture of solid materials or shaped bodies containing at least one zeolite and being at least partly crystalline. Furthermore, the present invention relates to the solid materials or shaped bodies as such and to the use of these materials for reactions of compounds having at least one C—C double bond with at least one hydroperoxide. Specifically, the present invention relates to a process for the manufacture of a solid material containing at least one zeolite and being at least partly crystalline, wherein the synthesis of the said solid material involves at least one partial step of contacting at least one transition metal oxide source with at least one epoxide or hydrolysate thereof prior to or during the at least partial crystallization of said solid material.

21 Claims, No Drawings

CATALYST FOR EPOXIDATION REACTIONS

The present invention relates to the manufacture of solid materials or shaped bodies containing at least one zeolite and being at least partly crystalline. Furthermore, the present invention relates to the solid materials or shaped bodies as such and to the use of these materials for reactions of compounds having at least one C—C double bond with at least one hydroperoxide. Specifically, the present invention relates to a process for the manufacture of a solid material containing at least one zeolite and being at least partly crystalline, wherein the synthesis of the said solid material involves at least one partial step of contacting at least one transition metal oxide source with at least one epoxide or hydrolysate thereof prior to or during the at least partial crystallization of said solid material.

The synthesis of solid materials containing at least Si and Ti, in particular of titanium zeolithes used for applications in catalysis, is of particular commercial importance and has resulted in a large body of prior art. By way of example, U.S. Pat. Nos. 4,666,692 and 4,410,501 are cited in the general context of the manufacture of titanium silicalites.

An integrated process for producing solid materials containing Si and Ti and shaped bodies produced therefrom is described, e.g. in WO 98/55229.

The scientific publication "*Studies of the synthesis of titanium silicalite, TS*-1" from A. Thangaraj et al. [Zeolites 12 (1992) 943 ff] relates to a procedure to obtain TS-1, wherein the precipitation of titanium oxide during the hydrolysis of the alkoxides in the synthesis mixture is minimized or avoided by adding, in a step separate step, isopropyl alcohol to the titanium source. Not only is it found that the amount of metal oxide precipitation indeed decreases, but also that more Ti is built into the silicalite framework. However, said publication is silent as to the use of other compounds to be added to a transition metal oxide source and is silent as to the effect such treatment has on the catalyst actually used in a chemical reaction, e.g. an epoxidation reaction.

Referring to said scientific publication, U.S. application Ser. No. 2001/0041162 A 1 describes the use of alcohols having a $pK_a$ value lower than that of water, more specifically the use of 2-ethoxyethanol, in order to avoid precipitation metal oxides such as anatase, from the synthesis solution. As a result it is found that indeed the molar fraction of precipitated Ti in anatase form is significantly reduced. However, no significant effect on important performance characteristics of the catalyst actually used for epoxidation reactions were identified, in particular on epoxide selectivity.

The object of the present invention was to provide a catalyst, and a process for the manufacture thereof, that results in improved performance characteristics of catalysts based on zeolite materials, in particular with respect to selectivity and activity, over the prior art.

Surprisingly, it has been found that by adding the epoxide that is the product of the desired catalyzed epoxidation reaction, or a hydrolysate thereof, to the transition metal oxide source, the performance characteristics of the catalyst obtained from the synthesis mixture comprising the transition metals oxide source so treated, is improved over a corresponding catalyst that had not been subjected to the inventive step of adding an epoxide or hydrolysate thereof to the transition metal oxide source.

The catalytic material (solid material or shaped body) obtainable by the inventive process of adding an epoxide or hydrolysate thereof can be used for any catalytic reaction in which it improves at least one reaction parameter or catalyst performance characteristic, such as selectivity, yield, activity, over the respective values obtained using catalytic material that has not been subjected to the inventive treatment of adding an epoxide or hydrolysate thereof to the transition metal oxide source.

Preferably, the catalytic material obtainable by the inventive process is used in reactions of compounds containing at least one C—C-double bounds with at least one hydroperoxide, i.e. in epoxidation reactions.

In the following, a glossary of the most important expressions used in the framework of the present invention are defined.

A "synthesis mixture" as used in the context of the present invention pertains to any mixture which yields, by means of crystallization, a mixture containing a solid material that is at least partially crystalline and a fluid material. Preferably, the synthesis mixture contains at least a Si source (Si precursor), a transition metal oxide source (transition metal precursor) and a mineralizing and/or structure forming agent. In particular, reference is made to all synthesis mixtures known to the expert in the field of zeolite preparation, particularly the hydrothermal treatment of gels. The synthesis mixture may be a sol, gel, solution, or a suspension. The synthesis mixture may be obtained by mixing two separate solutions.

"Zeolites" as used in the context of the present invention are crystalline alumosilicates with well-ordered channel or cage structures containing micropores. The expression "micromore" as used in the context of the present invention corresponds to the definition given in "Pure Applied Chemistry", Vol. 45, p. 71 ff., in particular p. 79 (1976). According to this definition, micropores are pores with a pore diameter of less than 2 nm. The network of these zeolites is made of $SiO_4$ and $AlO_4$-tetrahedra that are bridged via shared oxygen bonds. An overview of the known structures can be found in, example given, W. M. Meier und D. H. Olson in "Atlas of Zeolite Structure Types", Elsevier, $4^{th}$ Ed., London 1996. In addition to micropores, solid materials or shaped bodies according to the invention may contain mesopores or macropores as well.

"Solid materials" as obtained, for example, after the crystallization of the synthesis mixture, are to be understood in the context of the present invention as any known material which displays at least the following properties: (i) it contains at least one zeolite material and (ii) is different from the synthesis mixture described before in the sense that a separation of said solid material from its mother liquor is possible and/or concentrating of the solid material by, e.g., ultra-filtration is possible. Typically, the solid material prevails as particles suspended in the mother liquor.

A "mother liquor" in the context of the present invention is any liquid phase that may contain a unlimited number of substances dissolved therein, however in itself is not a solid material. In particular, the mother liquor may contain adjuvants dissolved therein. In the sense of the present invention, a mother liquor can only occur after step (I) of the integrated process as described above. Typically, a mother liquor is the liquid phase in which the solid material is suspended in the form of particles. Said mixture (I) is then subjected to step (II) of separating and/or concentrating of the solid material in mixture (I).

The term "epoxide" as used in the context of the present invention, refers to any compound with at least two adjacent carbon atoms, wherein at least those two carbon atoms are, at least partly, chemically bound to one mutual oxygen atom. By way of example, propylene oxide is mentioned. A "hydrolysate" of an epoxide is the product of the reaction of the epoxide with any compound leading to hydrolysis, e.g. water. By way of example, propylene glycol is mentioned as the hydrolysate of the above mentioned propylene oxide.

Step (II) of the present invention relates to concentrating and/or separating of the solid material in the mother liquor and/or from the mother liquor, wherein the mixture (I) containing the solid material is obtained from step (I). The term "concentrating and/or separating" is to be understood in the context of the present invention as any step that at least results in that at the end of step (II), the solid material content in the mixture is increased and/or the solid material is separated partly or entirely from the mother liquor.

The complete "separation" of the solid material from the mixture (the suspension) is explicitly contained in the definition of "concentrating" as an extreme case. Such methods of separating and/or concentrating include, but are only limited to, spray-drying or ultrafiltration and will be described in more detail below. The terms "filtration", "ultra-filtration", and "spray-drying" as well as other methods of concentrating and/or separating the solid material from the mother liquor are described in detail in DE 102 324 06.9, the respective content of which is hereby incorporated by reference.

A "shaped body" as used in the context of the present invention is to be understood to be any three dimensional entity, which can be obtained by any of the shaping steps (S) mentioned below. The shaped body is obtained in a typical manner by means of compacting of the solid material described above. Said solid material may originate from steps (II) and/or (III), using optional steps of calcining (C).

The expressions "granulating" and "agglomerating" as used in the context of the present invention are to be seen as synonymous and describe, respectively, any conceivable process that can be used to increase the diameter of the particles obtained from step (II). Said increase of the particle diameter can be achieved by baking the particles together or by growing on the particles layer by layer. The process of granulating thereby includes but is not limited to processes taking advantage of the phenomenon of wetting of the particles by at least one liquid. Furthermore, binding materials may be added to the mixture in order to enhance or enable the agglomerating and/or granulating of the particles.

A "binding material" as used in the context of the present invention is to be understood to be any material that enables a physical, chemical, or physical-chemical bond between the substances constituting the particle. Such binding materials may be used in the step (S) of shaping or forming the solid material into a shaped body as well. Reference is made to the description of binding materials in that context.

The inventive treatment of of adding an epoxide or hydrolysate thereof to the transition metal oxide source is preferably part of an integrated process, namely an integrated process producing a mechanically stable solid material or a shaped body containing at least one zeolite material. Schematically, such an integrated process can be characterized by the following steps:

(I) at least partial crystallization of at least one solid material containing at least one zeolite out of a synthesis mixture, resulting in mixture (I) containing at least said solid material and a mother liquor;

(II) separating and/or concentrating of the solid material from mixture (I);

(W) bringing the solid material from step (II) in contact with a composition containing water;

(III) agglomerating or granulating or agglomerating and granulating of the solid material from step (W);

wherein steps (W) and (III) are optional. Step (II) may additionally include the drying and/or washing of the solid material, possibly also in several iterations.

Additionally, and/or optionally the following steps may be part of the integrated process as well:

(S) shaping of the solid material into shaped bodies subsequent to steps (W) or (III);

(C) Calcining of the solid material and/or the shaped body at temperatures higher than 400° C.;

wherein the step (C) of calcining may be performed at least one after at least one of the following steps of the integrated process: (II), (W), or (III).

In a preferred embodiment, step (W) is performed after step (S) of shaping the solid material.

In the present application, the inventive solid material containing at least one zeolite material or the shaped body obtainable therefrom is discussed in the context of applications in the field of catalysis. This, however, cannot be construed as a limitation of the use of the solid material and/or the shaped body to the field of catalysis. The explicit discussion of examples in the field of catalysis is illustrative only. The inventive material may be used in other fields as well.

In the following, the individual steps of the integrated process for producing a solid material and/or shaped body are summarized, wherein the solid material and/or the shaped body contain at least one zeolite material and is/are at least partially crystalline. Of particular importance is the step (I) containing the inventive partial step (Ib).

Step I: (Partial) Crystallization of the Synthesis Mixture

According to the present invention, step (I) of the at least partial crystallization of at least one solid material containing at least one zeolite out of a synthesis mixture, resulting in mixture (I) containing at least said solid material and a mother liquor comprises at least the following partial steps:

(Ia) mixing of at least one hydrolyzable silicon source with a mineralizing and/or structuring agent and water;

(Ib) mixing of at least one transition metal oxide source with an epoxide or a hydrolysate thereof;

(Ic) mixing of the mixtures from (Ia) and (Ib) so that at least a part of the hydrolyzable compounds hydrolyzes;

(Id) distilling at least parts of the alcohol that has been formed as a result of the at least partial hydrolysation of at least part of the hydrolyzable compounds;

(Ie) adding water to the bottom of (Id);

(If) reacting of the synthesis mixture resulting from (Ie) at a temperature elevated with respect to room temperature.

Preferably, steps (Ia) and (Ib) are performed in separate containers.

In a preferred embodiment, the hydrolyzable silicon source comprises at least one silicon oxide, the mineralizing and/or structuring agent comprises at least one tetraalkylammonium hydroxide, the transition metal oxide source comprises at least one titanate and the epoxide or hydrolysate thereof comprises at least the epoxide or the hydrolysate thereof of the reaction for which the solid material is ultimately used as a catalyst.

In a further preferred embodiment, the hydrolyzable silicon source comprises at least tetraethoxy silicate, the mineralizing and/or structuring agent comprises at least tetrapropylammonium hydroxide, the transition metal oxide source comprises at least tetrabutylorthotitanate and the epoxide or the hydrolysate thereof comprises at least propylene oxide or propylene glycol, with propylene glycol being particularly preferred.

As far as the least one zeolite material resulting from said synthesis step (I) is concerned, no limitations exist. Preferably, a zeolite containing titanium, zirconium, chromium, niobium, iron, bor, vanadium is employed. Particularly preferred, a zeolite containing titanium is employed, wherein zeolites known to the expert in the field as "titanium silicates" (TS) are particularly preferred.

Such zeolites containing titanium, in particular those displaying a crystalline structure of the MFI-type as well as ways for producing them are described, for example, in WO 98/55228, WO 98/03394, WO 98/03395, EP-A 0 311 983, or EP-A 405 978. The respective content of these documents is hereby incorporated by reference. In addition to Si and Ti, said zeolite materials may contain additional elements, such as aluminum, zirconium, tin, iron, cobalt, nickel, gallium, bor, or small amounts of fluorine. It is preferred that the titanium of the zeolite is partly or completely replaced by vanadium, zirconium, or niobium, or any mixture of two or more of these components.

Zeolites containing titanium and displaying a MFI-structure are known to yield a characteristic pattern in x-ray diffraction. Furthermore, these materials display a vibration band in the infrared (IR) at approximately 960 cm$^{-1}$. Therefore, it is possible to distinguish the zeolites containing titanium from crystalline or amorphous $TiO_2$-phases or from alkaline metal titanates.

In a further preferred embodiment, the at least one zeolite material is selected from the following group: zeolites containing at least one of the following elements: titanium, germanium, tellurium, vanadium, chromium, niobium, zirconium, particularly those having a pentasil zeolite structure, in particular the structural types that can be, via x-ray diaction, assigned to the structure types of ABW-, ACO-, AEI-, AEL-, AEN-, AET-, AFG-, AFI-, AFN-, AFO-, AFR-, AFS-, AFT-, AFX-, AFY-, AHT-, ANA-, APC-, APD-, AST-, ATN-, ATO-, ATS-, ATT-, ATV-, AWO-, AWW-, BEA-, BIK-, BOG-, BPH-, BRE-, CAN-, CAS-, CFI-, CGF-, CGS-, CHA-, CHI-, CLO-, CON-, CZP-, DAC-, DDR-, DFO-, DFT-, DOH-, DON-, EAB-, EDI-, EMT-, EPI-, ERI-, ESV-, EUO-, FAU-, FER-, GIS-, GME-, GOO-, HEU-, IFR-, ISV-, ITE-, JBW-, KFI-, LAU-, LEV-, LIO-, LOS-, LOV-, LTA-, LTL-, LTN-, MAZ, MEI-, MEL, MEP-, MER-, MFI-, MES-, MON-, MOR-, MSO-, MTF-, MTN-, MTT-, MTW-, MWW-, NAT-, NES-, NON-, OFF-, OSI-, PAR-, PAU-, PHI-, RHO-, RON-, RSN-, RTE-, RTH-, RUT-, SAO-, SAT-, SBE-, SBS-, SBT-, SFF-, SGT-, SOD-, STF-, STI-, STT-, TER-, THO-, TON-, TSC-, VET-, VFI-, VNI-, VSV-, WIE-, WEN-, YUG-, ZON, as well as mixed structures of at least two or more of the aforementioned structures. Furthermore, it is conceivable to use zeolites containing titanium with the structure of ITQ-4, ITQ-9, SSZ-24, TTM-1, UTD-1, CIT-1 or CIT-5. Further zeolites containing titanium are such of the structure types ZSM-48 or ZSM-12.

Zeolites containing titanium of the structure MFI, MEL or MFI/MEL mixed structures, as well as MWW, BEA or mixed structures thereof are preferred in the context of the present invention. Further preferred in the context of the present invention are these zeolite catalysts containing titanium that are referred to, in general, as "TS-1", "TS-2" or "TS-3", as well as zeolites containing titanium displaying a structure that is isomorphous to β-zeolite.

If necessary, or advantageous, additional compounds may be added. The reaction or mixing of each partial step of step (I) is performed in an open container or in a pressure-tight container (autoclave), optionally at elevated temperatures, over the course of several hours or days. Thereby, a product that is at least partly crystalline is obtained.

As far as the duration of the inventive partial step is concerned, no limitations exist, so long as the partial step results in an improved performance of the catalyst over a catalyst that had not been subjected to that partial step. As a measure for the increased performance, improved activity, selectivity and/or yield may be used. Increased mechanical stability or improved properties that are otherwise relevant for the process of interest can be used as well. In a preferred embodiment, the inventive partial step (Ib) consists of mixing the transition metal oxide source with the epoxide or hydroxide and stirring until the solution is transparent to the eye.

Step (II): Separating and/or Concentrating

In step (II) the solid material is separated from the mother liquor and/or is concentrated in the mother liquor. Step (II) is performed with mixture (I) from step (I). Methods of separating and/or concentrating include but are not limited to the following: filtration, ultrafiltration, diafiltration, centrifuge methods, spray drying, spray granulating, etc.

This step (II) of concentrating and/or separating is preferably performed prior step (W) of bringing the solid material in contact with a composition containing water and after the step (I) of crystallizing the solid material. The purpose of step (II) is to increase the solid content in the mixture resulting from step (I). For details of filtration and/or concentration, reference is made to DE 10232406.9, the entire contents of which are hereby incorporated by reference.

Preferably, the solid material is concentrated first and then separated from the mother liquor by filtration. For example, the method of ultrafiltration may be used for concentrating the solid material in the retentate, while the solid material may be separated from all or parts of the mother liquor by means of conventional filtration. With respect to conventional filtration, all methods known to the expert in the art may be used such as cake filtration or methods involving a centrifuge.

In another preferred embodiment step (II) consists of-bringing an inert support body in contact with the synthesis mixture from step (I). As far as the "inert support body" is concerned, no limitations exist, so long as the inert support body does not react noticeably with the synthesis mixture or any component thereof and said inert support body is capable of accommodating, at least partly, the solid material contained in the synthesis mixture from step (I), preferably in the form of a (thin) film. Such inert support bodies may include but are not limited to: beads or pellets made form technical ceramic materials such as alumosilicate ceramics, alkali alumosilicate ceramics, aluminum oxide based ceramics (e.g. mullit), magnesium silicates (e.g. steatit, cordierit). The use of steatit or mullit is preferred. Said inert support bodies may be porous or dense, wherein the use of dense support bodies is preferred.

Said support bodies may be brought in contact with the synthesis mixture from step (I) by means of all methods known to expert in the context of bringing a solid body in contact with a fluid medium. Spraying of the synthesis mixture onto the support bodies, dipping the support bodies into the synthesis mixture or saturating/soaking of the inert support bodies in the synthesis mixture are preferred. In case the method of bringing in contact is soaking/dipping/saturating, in a preferred embodiment, the soaked/dipped/saturated support bodies are exposed to an atmosphere with a partial pressure of the liquid medium of the synthesis mixture (e.g. water) lower than the pressure of the pure liquid, so that the liquid medium may, at least partly, evaporate.

As a result of said step of bringing inert support bodies in contact with the synthesis mixture from step (I), a (thin) film containing the solid material containing at least one zeolite and being at least partly crystalline forms on the support body and/or in the pores, if the support body is porous. The thickness of the film so formed may range from 1 µm to 1500 µm. In a preferred embodiment, the thickness of the film ranges from 5 µm to 50 µm. The result of this embodiment is referred to a "solid material" in the context of the present application and is processed the same way the solid material obtained by spray drying or ultrafiltration.

The solid material obtained after step (II) may now be optionally subjected to at least one step of washing and to at least one step of drying of the solid material. Furthermore, after the at least one step of drying, the solid material may also be calcined at temperatures of 400° C. and higher (see description of the step (C) of calcining given below).

Step (W): Treatment of the Solid Material with a Composition Containing Water

Subsequent to step (II) of concentrating and/or separating, the solid material may be subjected to a treatment of bringing the solid material in contact with a composition containing water.

As far as the term "bringing in contact" is concerned, any method is conceivable, in which the solid material is brought in physical contact with a composition containing water. This includes, but is not limited to: forming a slurry, suspension or mixture of the solid material in or with the composition containing water, the composition being preferably in a liquid phase, spraying the solid material with the composition containing water, subjecting the solid material to the composition containing water in the form of vapor and/or steam. It is particularly preferred to form a slurry of the solid material with the composition containing water in a stirring tank.

Preferably, the same stirring tank is used for step (W) that has already been used for crystallizing the solid material out of the synthesis mixture. In order to further the physical contact between the solid phase and the composition containing water, any means for stirring or otherwise mechanically acting the mixture containing the solid material and the composition containing water known to the expert in this field can be employed. Other methods of mixing and/or agitating, such as ultrasound agitation, magnetic stirring and the like are conceivable as well. Preferably the slurry of the solid material is brought in contact with a composition containing water in a tank vessel with a mechanical stirring device.

As far a the composition containing water is concerned, any substance can be used that contains, at least in parts, water in any of its modifications. These modifications include the liquid phase, the solid phase, vapor steam, super critical water. Furthermore, the water may by mixed with other substances. Preferably water is-used as such in the liquid phase or as steam. If water is used in the liquid phase, deionized water is preferred. Any method to deionize water known to the expert in the art is included, such as distillation or removing of electrolytes over an ion exchanger. While not preferred, the use of water containing salt and/or of water that is acidic or basic is conceivable as well.

For specific applications, bringing the solid material in contact with an aqueous ammonia solution may be preferred. In this case, a solution of ammonia in water is preferred, wherein the content of ammonia in water, given in % by weight with respect to the total weight, ranges from 5 to 60, preferably from 10 to 30. If a composition containing water and ammonia is used, step (W) is preferably performed at pressures elevated with respect to ambient pressure and not exceeding several hundred bars.

As far as the ratio, given in weight-percent, between the amount of solid material and the composition containing water is concerned, no principal limitations exist, save for the fact that the mixture or slurry should have viscous or hydraulic properties conducive to mechanical stirring.

Furthermore, it is preferred that the treatment of bringing the solid material in contact with a composition containing water is performed at a temperature elevated with respect to room temperature. Temperatures between room temperature and 750° C. are preferred. Temperatures between 100° C. and 250° C. are particularly preferred, while temperatures between 120° C. and 175° C. are further preferred.

The treatment (W) of the solid material with a composition containing water can be performed with any type of solid material. The solid material may be the material obtained from step (II) without drying or calcining. However, it is preferred that the solid material from step (II) has been dried and/or calcined before the treatment. It is further preferred, that the solid material has been washed, dried and optionally calcined prior to step (W). It is further preferred that the solid material has been obtained by spray granulation and/or ultrafiltration (in conjunction with conventional filtering).

After the optional step (W) has been performed, i.e. after the solid material has been brought into contact with the composition containing water, the composition containing water may be removed from the solid material and/or the solid material may be concentrated in the composition containing water. To achieve this end, step (II) may be repeated. This is, the mixture containing the solid material and composition containing water may be subjected to, example given, sprayed drying, ultrafiltration, or ultrafiltration in conjunction with conventional filtration. It may be only subjected to conventional filtration as well.

Step (III): Agglomerating/Granulating

Subsequent to step (W), the solid particles can be increased in their size using any method of agglomerating and/or granulating known to the expert in the field. For a list of methods used in this context, reference is made to DE 10232406.9, the respective contents of which are hereby incorporated by reference.

Post-treatment

In order to improve the catalytic performance of the end product, subsequent to step (W) or to step (III) or subsequent to both, it is optionally possible to perform at least one step of post-treatment of the material, including but not limited to the following steps: drying, washing, calcining, treating of the solid material with a hydrogen peroxide solution. Any combination of these steps is conceivable as well. It is also possible to treat this solid material containing at least one zeolite material with compounds containing alkaline metal, in order to transform the zeolitic material from the H-form into the cationic form. The solid material obtained after step (W) or after step (III) or after any of the two steps in conjunction with any of the steps of post treatment mentioned here, can then be processed further to a shaped body, as described below.

Step (S): Shaping of the Solid Material

The starting point for the process to produce a shaped body containing zeolite is either the solid material after step (II) or the solid material after step (W) or the solid material after step (III), optionally involving any of the steps of post-treatment mentioned in the proceeding paragraph. As it has been mentioned above, if the process so far has involved at least one step (W) of bringing the solid material in contact with a composition containing water, the material obtained after step (S) does not need to be subjective to an step (W). However, if the solid material so far has not been subjected to the treatment (W), the step of bringing the shaped body in contact with at least one composition containing water has to be performed after the step (S) of shaping the solid material or after said step (S) in conjunction with a step (C).

In any case, the step (S) of shaping the solid material involves at least one step of forming a three dimensional material that contains at least one zeolite material. As far as this specific (at least one) step of shaping the solid materials is concerned, reference is made to WO 98/55229 and to DE 10232406.9 whose respective content is incorporated into the present application by reference.

Preferably, a binding material is added to the solid material resulting from any of the steps mentioned above. Further adjuvants that may be added to the solid material prior to the step (S) include but are not limited to: mixtures containing at least one alcohol and water, if suitable one or more organic substances increasing the viscosity, and further substances known from the prior art.

Preferably, the solid material is milled and mixed with silica sol, a dispersion of polystyrene, cellulose and polyethylene oxide (PEO), as well as with water. Said mixture is homogenized in any type of kneading apparatus. In lieu of kneading, any method of bringing the substances into physical contact may be used. Preferably, the mass obtained by this method shows plastic flow. The shaped body can then be obtained from this mass, example given, by means of molding, in particular extrusion molding, or by any other method of extrusion known to the expert in the field.

As far as the binding materials are concerned, in principle, every substance can be used that achieves cohesion between the particles that is increased over the cohesion achieved without the presence of the binding material. Preferred binding materials are selected from the following group consisting of: hydrated silica gel, silicic acid, tetraalkoxy silicates, tetraalkoxy titanates, tetraalkoxy zirconates or mixtures of two or more of the afore-mentioned substances. Tetraalkoxy silicates such as tetramethoxy silicates, tetraethoxy silicates, tetrapropoxy silicates or tetrabutoxy silicates are preferred. Tetramethoxy silicates or tetraethoxy silicates and silica sols are particularly preferred.

Further preferred binding materials are amphiphilic substances, i.e. molecules with a polar and a non-polar part. The use of graphite is conceivable as well. As far as further binding materials are concerned, reference is made to WO 98/55229 and to DE 10232406.9 whose respective content is incorporated into the present application by reference.

Said binding materials can be used either alone or as mixtures of two or more of these, or they can be used together with other materials to be used for enabling or enhancing the binding of materials containing zeolite, such as oxides of silicate, bor, phosphor, zirconium, and/or titanium. By way of example, clays are also to be mentioned.

In the process of shaping the solid material into a shaped body, up to approximately 80% by weight of binding materials with respect to the total mass of the shaped body are to be used. It is preferred to use from approximately 10 to approximately 75% by weight of binding materials, while using 25% to approximately 45% is particularly preferred.

In the framework of the process to produce a shaped body, polymers may be added with the intent to create pores of a certain size, a certain volume or a certain size distribution. In the context of the present invention, polymers are preferred that can be dispersed, emulsified or suspended in aqueous solvents. Said at least one polymer is preferably selected from the group of polymer vinyl compounds, such as polystyrene, polyacrylates, polymethacrylates, polyolefins, polyamids, or polyesters. These polymers are removed from the shaped bodies after the process of forming and/or shaping by means of calcining the shaped body. If polymers are added, the content of polymer during the production of the shaped body amounts to from approx. 5 to approx. 90% by weight, preferably from approx. 15 to approx. 75% by weight, wherein a content ranging from 25 to 55% by weight is particularly preferred. The amounts given in weight-% refer to the amount of polymer in the solid material containing zeolite, respectively.

Furthermore, it is preferred to add a pasting agent. As far as the pasting agent is concerned, any substances known from the prior art to improve the mixing, kneading, or flow properties of the mass can be used. Preferably, organic hydrophilic polymers are used, such as cellulose, starch, polyacrylates, polymethacrylates, polyvinylalcohol, polyvinyl pyrrolidon, polyisobutene, polytetrahydrofuran. Primarily, these substances enable or improve the formation of a plastic mass during the process of kneading, forming, and/or drying by means of bridging the primary particles. Moreover, these adjuvants enable or enhance the mechanical stability of the shaped body during the steps of forming or drying.

These substances are removed from the shaped body by means of calcining after the step of shaping. Further adjuvants are described in EP-A 0 389 041, EP-A 0 200 260, and in WO 95/19222, the entire contents of which are hereby incorporated by reference.

In a preferred embodiment, after having added the binding material to the solid material containing at least one zeolite, the organic substance increasing viscosity is added and the mass is homogenized for 10 to 180 minutes in the kneading apparatus or in the extruder. The temperature applied to the mass is typically about 10° C. under the boiling point of the pasting agent. The pressure is either ambient pressure or is slight over-pressure. In principle, the order of adding additional components to the solid material and the binder is not believed to be critical. The mass obtained as described above is kneaded until a plastic mass can be extruded.

In the context of the present invention, those methods for forming a shaped body from a solid material are preferred, in which the forming can be performed in commercially available extruders. Preferably, extrudates of a diameter ranging from approx. 1 to approx. 10 mm are used, particularly preferred are extrudates with diameters ranging from approx. 2 to approx. 5 mm. Extruders that can be used in the context of the steps described here are described, for example, in "Ullmann's Enzyklopädie der Technischen Chemie", $4^{th}$ Edition, Vol. 2, p. 205 ff. (1972).

In principle, all methods of shaping and of forming that are known to the expert in the art can be used. Next to extrusion, other known methods, are briquetting, spelleting, pressing, sintering, or roasting.

The technique of co-extruding can be employed as well. Here, two materials are co-extruded simultaneously. Preferably the aforedescribed active material (solid material according to the invention) is extruded together with an inert material, i.e. a material that does not react noticeably with the active material. Preferably, the matrix of the extruder is designed so that the active material is extruded as a layer on the inert material. Therefore, strands result, whose core is made of the inert material and whose outer layer is the active solid material. In a preferred embodiment, the thickness of the active layer ranges from 1 to 1500 $\mu$m, preferably from 5 to 50 $\mu$m.

The use of binding materials or other adjuvants is in any event optional. The materials to be compacted may be dry or moist or may prevail as a slurry.

The step of shaping and/or forming can be performed at ambient pressure or at a pressure that is elevated with respect to ambient pressure, for example, in a pressure range from 1 bar to 700 bars. Furthermore, the shaping and/or forming can be performed at ambient temperature or at a temperature increased with respect to ambient temperature, example given, a temperature which is ranging from 20° C. to approx. 300° C. If drying and/or sintering is part of the shaping and/or forming step, temperatures of up to 1500° C. are conceivable. Furthermore, the step of compacting and of forming can be performed at ambient atmosphere or in a controlled atmosphere. Controlled atmospheres include but are not limited to inert gas atmospheres, reducing atmospheres, or oxidizing atmospheres.

Post-treatment of the Shaped Body

After forming and/or shaping (S) the shaped bodies, they are typically dried at temperatures ranging from approx. 30° C. to approx. 140° C. for a time interval ranging, typically from 1 h to 20 h. Subsequent to this step, the shaped body is calcined at temperatures ranging from approx. 400° C. to approx. 800° C. and for a time interval ranging from approx. 3 h to approx. 10 h. Calcining can be performed at ambient pressure, preferably in air or in a mixture containing air or under inert conditions.

In another step of post-treatment, the extrudates obtained as described above may be milled and/or crushed. The milling and/or crushing preferably leads to a granulate with an average particle diameter ranging from 0.1 to approx. 5 mm. Particle diameters ranging from approx. 0.5 to 2 mm are particularly preferred.

Subsequent to the step (S) or subsequent to said step (S) in conjunction with any step of post-treatments such as (in particular) drying and calcining, the treatment of bringing the solid material, in this case a shaped body, in contact with a material containing water, i.e., the step (W) may be performed.

If the step (W) is performed at this point, i.e. after the step (S) or the steps (S) and (C) in conjunction, everything that has been disclosed before about the specific embodiments of said step of (W) is valid here as well. In a preferred embodiment, however, the shaped body is charged into the reactor that is used for the desired reaction, typically an epoxidation reaction, and said shaped body, is subjected to the treatment with the composition containing water, in the reactor. Preferably the treatment consists in exposing and/or bringing in contact of the shaped body with water steam.

In addition to the process for producing a solid material and/or a shaped body as described above, the present invention also relates to the respective material or shaped body as such.

In particular, the solid material according to the invention is obtainable by a sequence of the following steps:

(I) at least partial crystallization of at least one solid material containing at least one zeolite out of a synthesis mixture, resulting in mixture (I) containing at least said solid material and a mother liquor;

(II) separating and/or concentrating of the solid material from mixture (I);

(W) bringing the solid material from step (II) in contact with a composition containing water;

(III) agglomerating or granulating or agglomerating and granulating of the solid material from step (W);

wherein the steps (III) and (W) are optional Step (II) may additionally include the drying and/or washing of the solid material, possibly also in several iterations.

Here, the inventive partial step (Ib) is part of the above mentioned step (I):

(Ia) mixing of at least one hydrolyzable silicon source with a mineralizing and/or structuring agent and water;

(Ib) mixing of at least one transition metal oxide source with an epoxide or a hydrolysate thereof;

(Ic) mixing of the mixtures from (Ia) and (Ib) so that at least a part of the hydrolyzable compounds hydrolyzes;

(Id) distilling at least parts of the alcohol that has been formed as a result of the at least partial hydrolysation of at least part of the hydrolyzable compounds;

(Ie) adding water to the bottom of (Id);

(If) reacting of the synthesis mixture resulting from (Ie) at a temperature elevated with respect to room temperature.

Furthermore, the present invention relates to a shaped body obtained from the solid material described above. The shaped body is obtained by subjecting the solid material to a step (S) of shaping, as described in detail above, and (optionally) to a step (C) of calcining. The sequence of the steps is schematically shown below:

(I) at least partial crystallization of at least one solid material containing at least one zeolite out of a synthesis mixture, as described above in (Ia) to (If), resulting in mixture (I) containing at least said solid material and a mother liquor;

(II) separating and/or concentrating of the solid material in mixture (I);

(III) agglomerating or granulating or agglomerating and granulating of the solid material from step (W);

(S) shaping of the solid material from step (II) or (III)

Hereby, the following step (W) can optionally be performed after step (II) or after step (S) or after step (II) and after step (S):

(W) bringing the shaped body from step (S) in contact with a composition containing water;

Finally the present invention relates to the use of the inventive materials, i.e. the solid material and/or the shaped bodies as catalysts. The materials obtainable by the inventive process or the materials obtained by the inventive process are particularly suited for catalytic reactions involving compounds with at least one C—C-double bond. Particularly preferred is the reaction of at least one compound containing at least one C—C-double bound with at least one hydrogen peroxide. These reactions are also referred to as epoxidation reactions. As far as further possible reactions are concerned for which said catalysts maybe employed, reference is made to DE 102 32 406.9 the respective contents of which (in particular pages 27 and 28) are hereby incorporated by reference.

EXAMPLE C 1

Comparative Example

In a four neck flask, 658 g of tetraethoxysilane are mixed with 20.8 g of tetraethylorthotitanate. While stirring, a solution of 340 g of tetrapropylammoniumhydroxide (40% by weight, in water) and 563 g of deionized water is added slowly thereto.

The solution is stirred at room temperature for one hour. Subsequently, the alcohol formed due to hydrolysis is distilled at a bottom temperature of 92° C. The bottom (915 g) is filled with water to 1600 g.

This batch is reacted in a steel autoclave at 175° C. and for 24 hours while being stirred. After the mixture has cooled down, it consists of a white suspension. Therefrom, the solid material is filtrated, rinsed with water and dried at 120° C. for 24 hours. Subsequently, said material is calcined in air two times for 5 hours, respectively, at a temperature of 450° C.

The yield in isolated solid material is 190 g. The content in Ti of the zeolite of MFI-structure thus obtained is 2.1% by weight.

The following test of the catalytic material as described above has been performed: In a pressure-tight glass reactor, 0.5 g of said catalyst was mixed with 45 ml of methanol. At a temperature of 0° C., 20 ml of propylene were dosed in and subsequently, by means of a pump, 18 g of hydrogen peroxide (30% by weight, in water; Merck) were metered in. After a reaction time of 5 hours, the mixture is expanded (pressure relieved) and the liquid phase is analyzed by means of gas chromatography. The reaction mixture contains 8.7% by weight of propylene oxide.

EXAMPLE C 2

The catalyst material as described above is shaped into a shaped body according to the following procedure: 60 g of the inventive solid material as described in Example C 1 are milled and mixed with the following substances: 56.5 g of silica sol (Ludox AS 40% by weight $SiO_2$), a total amount of 32.9 g of a polystyrene dispersion (43.5 weight % of polymer), 2.7 g of methyl cellulose (Walocel) and 0.88 g of polyethylene oxide (PEO). 20 g of water are added to the mass. Said mass is homogenized in a kneading apparatus.

However, the materials are not added at the same time. Specifically, during the process of kneading, the polystyrene dispersion is added within 5 minutes, and after 10 minutes the silica sol is added slowly. After 10 further minutes of kneading, the PEO is added and gobbled for a further 10 minutes. Subsequently, water is added in portions of 5 ml, respectively.

The paste so obtained is formed after a total of 60 minutes of kneading and at a extrusion pressure of 70 bars via a extruder having a matrix of 1.5 mm holes. This way the solid material is alternately formed into strands.

The shaped body obtained this way is dried for four hours at 120° C. (heating ramp of 2 K per minute) Finally, the shaped body is calcined at 490° C. for four hours (heating ramp 1 K per minute). The atmosphere is air. The yield is 65.24 g. The content in titainium of the shaped body produced this way is 1.4% by weight.

Said shaped body was subjected to a long term test for selectivity: 13.5 g of the shaped bodies were loaded into a tube reactor (1.3 m length). The catalyst was exposed at a pressure of about 20 bars to a feed of 48 g/hour of methanol, 8.2 g/hour of hydrogen peroxide (40% by weight) and 4.7 g/hour of propylene (96% by volume of propylene). Temperatures were regulated between 20 and 40° C.

The analysis of the product mixture emerging from the reactor results in that after 230 hours, the selectivity for propylene oxide (with respect to $H_2O_2$) was 91%. The formation of oxygen (selectivity with respect to $H_2O_2$) was measured to be 2.4% and the unwanted side product methoxy propanol was formed with a selectivity of 3.3%.

EXAMPLE 1
Catalyst According to the Present Invention

In a four neck flask, 613 g of tetraethoxysilane are mixed with a solution of 316 g of tetrapropylammoniumhydroxide (40% by weight, in water) and 523 g of deionized water.

Separately, 18.1 g of tetrabutylorthotitanate are dissolved in 109 g of propylene glycol until a clear solution forms.

Said solution is dosed dropwise into the mixture of tetraethoxysilane and tetrapropylammoniumhydroxide described above. The resulting solution is stirred for 30 minutes. Subsequently, the alcohol formed due to hydrolysis is distilled at a bottom temperature of 92° C. The bottom (953 g) is filled with water to 1600 g.

This batch is reacted in a steel autoclave at 175° C. and for 24 hours while being stirred. The cooled down mixture consists of a white suspension. Therefrom, the solid material is filtrated, rinsed with water and dried at 120° C. for 24 hours. The yield of dried product was 209 g Subsequently, said material is calcined in air two times for 5 hours, respectively, at a temperature of 450° C. The mass loss due to calcination was measured to be 13% by weight.

The content in Ti of the zeolite of MFT-structure thus obtained is 1.9% by weight.

The following test of the catalytic material as described above has been performed: In a pressure-tight glass reactor, 0.5 g of said catalyst was mixed with 45 ml of methanol. At a temperature of 0° C., 20 ml of propylene were dosed in and subsequently, by means of a pump, 18 g of hydrogen peroxide (30% by weight, in water; Merck) were metered in. After a reaction time of 5 hours, the mixture is expanded (pressure relieved) and the liquid phase is analyzed by means of gas chromatography. The reaction mixture contains 9.7% by weight of propylene oxide. Despite the lower content in Ti of the zeolite, the inventive catalyst is shown to be significantly more active than the respective catalyst from the comparative example C 1.

EXAMPLE 2
Catalyst According to the Present Invention

The catalyst material as described in Example 1 is shaped into a shaped body according to the following procedure: 60 g of the inventive solid material as described in Example 1 are milled and mixed with the following substances: 56.5 g of silica sol (Ludox AS 40% by weight $SiO_2$), a total amount of 32.9 g of a polystyrene dispersion (43.5 weight % of polymer), 2.7 g of methyl cellulose (Walocel) and 0.88 g of polyethylene oxide (PEO). 20 g of water are added to the mass. Said mass is homogenized in a kneading apparatus.

However, the materials are not added at the same time. Specifically, during the process of kneading, the polystyrene dispersion is added within 5 minutes, and after 10 minutes the silica sol is added slowly. After 10 further minutes of kneading, the PEO is added and gobbled for a further 10 minutes. Subsequently, water is added in portions of 5 ml, respectively.

The paste so obtained is formed after a total of 60 minutes of kneading and at a extrusion pressure of 70 bars via a extruder having a matrix of 1.5 mm holes. This way the solid material is alternately formed into strands.

The shaped body contained this way is dried for four hours at 120° C. (heating ramp of 2 K per minute). Finally, the shaped body is calcined at 490° C. for four hours (heating ramp 1 K per minute). The atmosphere is air. The yield is 65.24 g. The content in titainium of the shaped body produced this way is 1.1% by weight.

Said shaped body was subjected to a long term test for selectivity: 13.5 g of the shaped bodies were loaded into a tube reactor (1.3 m length). The catalyst was exposed at a pressure of about 20 bars to a feed of 48 g/hour of methanol, 8.2 g/hour of hydrogen peroxide (40% by weight) and 4.7 g/hour of propylene (96% by volume of propylene). Temperatures were regulated between 20 and 40° C.

The analysis of the product mixture emerging from the reactor results in that after 215 hours, the selectivity for propylene oxide (with respect to $H_2O_2$) was 95.3%. The formation of oxygen (selectivity with respect to $H_2O_2$) was measured to be 0.6% and the unwanted side product methoxy propanol was formed with a selectivity of 2.4%.

Therefore, the catalyst of the invention not only shows increased activity over a catalyst that has not been subjected to the inventive partial step, but is otherwise obtained the same way, but also improved selectivity.

We claim:

1. Process for preparing a solid material containing at least one zeolite and being at least partly crystalline comprising a step (I), which step comprises at least partial crystallization of at least one solid material containing at least one zeolite out of a synthesis mixture, wherein said at least partial crystallization comprises contacting at least one transition metal oxide source with at least one epoxide or hydrolysate thereof prior to or during the at least partial crystallization.

2. Process according to claim 1, wherein step (I) comprises at least the following steps:
   (Ia) mixing of at least one hydrolyzable silicon source with a mineralizing and/or structuring agent and water;
   (Ib) mixing of at least one transition metal oxide source with an epoxide or a hydrolysate thereof;
   (Ic) mixing of the mixtures from (Ia) and (Ib) so that at least a part of the hydrolyzable compounds hydrolyzes;
   (Id) distilling at least parts of the alcohol that has been formed as a result of the at least partial hydrolysation of at least part of the hydrolyzable compounds;
   (Ie) adding water to the bottom of (Id);
   (If) reacting of the synthesis mixture resulting from (Ie) at a temperature elevated with respect to room temperature.

3. Process according to claim 2, wherein the hydrolyzable silicon source comprises at least one silicon oxide, the mineralizing and/or structuring agent comprises at least one tetraalkylammonium hydroxide, the transition metal oxide source comprises at least one titanate and the epoxide or hydrolysate thereof comprises at least the epoxide or the hydrolysate thereof of the reaction for which the solid material is ultimately employed as a catalyst.

4. Process according to claim 3, wherein the hydrolyzable silicon source comprises at least tetraethoxy silicate, the mineralizing and/or structuring agent comprises at least tetrapropylammonium hydroxide, the transition metal oxide source comprises at least tetrabutylorthotitanate and the epoxide or the hydrolysate thereof comprises at least propylene oxide or propylene glycol.

5. Process according to any of claim 1, wherein the at least one zeolite belongs to at least one of the following structure classes: MFI, MEL, MWW, BEA and any mixed structures thereof.

6. Integrated process for the production of a solid material containing at least one zeolite, comprising at least the following steps:
   (I) at least partial crystallization of at least one solid material containing at least one zeolite out of a synthesis mixture, resulting in mixture (I) containing at least said solid material and a mother liquor, said at least partial crystallization comprising at least the following steps:
      (Ia) mixing of at least one hydrolyzable silicon source with a mineralizing and/or structuring agent and water;
      (Ib) mixing of at least one transition metal oxide source with an epoxide or a hydrolysate thereof;
      (Ic) mixing of the mixtures from (Ia) and (Ib) so that at least a part of the hydrolyzable compounds hydrolyzes;
      (Id) distilling at least parts of the alcohol that has been formed as a result of the at least partial hydrolysation of at least part of the hydrolyzable compounds:
      (Ie) adding water to the bottom of (Id);
      (If) reacting of the synthesis mixture resulting from (Ie) at a temperature elevated with respect to room temperature;
   (II) separating and/or concentrating of the solid material in mixture (I).

7. Integrated process according to claim 6, wherein, after step (II), at least one of the following two additional steps is performed:
   (W) bringing the solid material from step (II) in contact with a composition containing water;
   (III) agglomerating or granulating or agglomerating and granulating of the solid material from step (W) or from step (II).

8. Integrated process according to claim 7, wherein, after step (W), a repetition of step (II) is performed.

9. Integrated process according to claim 7, wherein after at least one of the steps (I), (W) or (III), a step (C) of calcining the solid material is performed.

10. Integrated process according to claim 6, wherein after step (II), a step (C) of calcining the solid material is performed.

11. Integrated process as claimed in claim 6, wherein the hydrolyzable silicon source comprises at least one silicon oxide, the mineralizing and/or structuring agent comprises at least one tetraalkylammonium hydroxide, the transition metal oxide source comprises at least one titanate and the epoxide or the hydrolysate thereof of the reaction for which the solid material is ultimately employed as a catalyst.

12. Integrated process as claimed in claim 11, wherein the hydrolyzable silicon source comprises at least tetraethoxy silicate, the mineralizing and/or structuring agent comprises at least tetrapropylammonium hydroxide, the transition metal oxide source comprises at least tetrabutylorthotitanate and the epoxide or the hydrolysate thereof comprises at least propylene oxide or propylene glycol.

13. Integrated process for the production of a shaped body containing at least one zeolite, comprising at least the following steps:
   (I) at least partial crystallization of at least one solid material containing at least one zeolite out of a synthesis mixture, resulting in mixture (I) containing at least said solid material and a mother liquor, said at least partial crystallization at least the following steps:
      (Ia) mixing of at least one hydrolyzable silicon source with a mineralizing and/or structuring agent and water;
      (Ib) mixing of at least one transition metal oxide source with an epoxide or a hydrolysate thereof;
      (Ic) mixing of the mixtures from (Ia) and (Ib) so that at least a part of the hydrolyzable compounds hydrolyzes;
      (Id) distilling at least parts of the alcohol that has been formed as a result of the at least partial hydrolysation of at least part of the hydrolyzable compounds;
      (Ie) adding water to the bottom of (Id);
      (If) reacting of the synthesis mixture resulting from (Ie) at a temperature elevated with respect to room temperature;
   (II) separating and/or concentrating of the solid material in mixture (I);
   (III) agglomerating or granulating or agglomerating and granulating of the solid material;

(S) shaping of the solid material from step (II) or (III).

14. Integrated process according to claim 13, wherein the following step (W) is performed after step (II) or after step (S) or after step (II) and after step (S):
(W) bringing the solid material from step (II) or the shaped body from step (S) in contact with a composition containing water.

15. Integrated process as claimed in claim 14, wherein after at least one of the steps (II), (W), (III), or (S), a step (C) of calcining the solid material or the shaped body or the solid material and the shaped body is performed.

16. Integrated process according to claim 15, wherein said step of calcining is performed at temperatures higher than 400° C.

17. Integrated process according to claim 13, wherein the at least one step of shaping the solid material is selected from the group consisting of pelletizing, pressing, extruding, sintering, roasting, and briquetting.

18. Integrated process according to claim 17, wherein before and during or before or during the step of (S) of shaping the solid material, a binding material is added to said solid material.

19. Integrated process as claimed in claim 13, wherein the hydrolyzable silicon source comprises at least one silicon oxide, the mineralizing and/or structuring agent comprises at least one tetraalkylammonium hydroxide, the transition metal oxide source comprises at least one titanate and the epoxide or hydrolysate thereof comprises at least the epoxide or the hydrolysate thereof of the reaction for which the solid material is ultimately employed as a catalyst.

20. Integrated process as claimed in claim 19, wherein the hydrolyzable silicon source comprises at least tetraethoxy silicate, the mineralizing and/or structuring agent comprises at least tetrapropylammonium hydroxide, the transition metal oxide source comprises at least tetrabutylorthotitanate and the epoxide or the hydrolysate thereof comprises at least propylene oxide or propylene glycol.

21. Integrated process as claimed in claim 13, wherein after at least one of the steps (II), (III), or (S), a step (C) of calcining the solid material or the shaped body or the solid material and the shaped body is performed.

* * * * *